United States Patent [19]
Jans et al.

[11] Patent Number: 5,824,336
[45] Date of Patent: Oct. 20, 1998

[54] CHEWABLE FLUBENDAZOLE TABLETS FOR COMPANION ANIMALS

[75] Inventors: Eugene Maria Jozef Jans, Meerhout; Paul Marie Victor Gilis, Beerse, both of Belgium

[73] Assignee: Janssen Pharmaceutica, N.V., Beerse, Belgium

[21] Appl. No.: 732,263

[22] PCT Filed: May 12, 1995

[86] PCT No.: PCT/EP95/01801

§ 371 Date: Oct. 31, 1996

§ 102(e) Date: Oct. 31, 1996

[87] PCT Pub. No.: WO95/31963

PCT Pub. Date: Nov. 30, 1995

[30] Foreign Application Priority Data

May 20, 1994 [EP] European Pat. Off. .............. 94201434

[51] Int. Cl.⁶ ..................................................... A61K 9/20
[52] U.S. Cl. ........................... 424/441; 424/442; 424/465
[58] Field of Search ................................... 424/441, 442, 424/465

[56] References Cited

U.S. PATENT DOCUMENTS

| | | | |
|---|---|---|---|
| 4,578,268 | 3/1986 | Quinlan | 424/79 |
| 5,036,069 | 7/1991 | Andrews et al. | 514/269 |

*Primary Examiner*—Thurman K. Page
*Assistant Examiner*—D. Faulkner
*Attorney, Agent, or Firm*—Charles J. Metz

[57] ABSTRACT

The present invention relates to compositions comprising flubendazole of formula (I), which are palatable to companion animals, especially dogs.

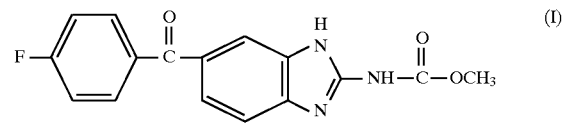

These find utility as palatable anthelmintic compositions for the treatment of helminthiasis.

7 Claims, No Drawings

CHEWABLE FLUBENDAZOLE TABLETS FOR COMPANION ANIMALS

CROSS REFERENCE TO RELATED APPLICATIONS

This application is based upon PCT Application Serial No. PCT/EP 95/01801, filed May 12, 1995.

The present invention relates to compositions comprising flubendazole, which are palatable to companion animals, especially dogs. These compositions find utility as palatable anthelmintic compositions for the treatment of helminthiasis.

Flubendazole is an anthelmintically active compound having the formula (1).

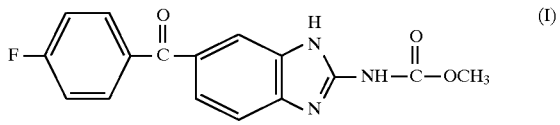

Flubendazole is the generic name of methyl [5-(4fluorobenzoyl)-1$\underline{H}$-benzimidazol-2-yl]carbamate. Flubendazole has been described in U.S. Pat. No. 3,657,267. Methods of preparing said compound are also mentioned in said patent. The anthelmintic activity has already been described extensively and the product has been on the market for many years as a veterinary pharmaceutical under the brand names Flubenol®, Biovermin®, Flubenol KH®, Flumoxal®, Flutelmium®.

Over the years, owners of companion animals and veterinarians have continually made the remark that the available tablets, pills or formulated compositions marketed for admixture of flubendazole with feeds are not completely satisfactory. This has resulted in the reluctance of the animals to ingest said tablets, pills or feed containing medication. It would therefore be highly advantageous and most desirable if flubendazole could be rendered palatable without destroying its efficacy. Furthermore, it would be most advantageous if a palatable composition containing flubendazole could be prepared in the form of a chewable tablet, pill, granulated product or the like, especially a chewable tablet It is therefore an object of this invention to provide palatable, therapeutically effective compositions containing flubendazole, useful for the treatment of helminthiasis in companion animals, especially dogs.

It is also an object of the present invention to provide methods for preparing compositions containing flubendazole which are palatable for companion animals, especially dogs.

Compositions according to the present invention will preferably comprise besides active ingredient pharmaceutically acceptable carriers and excipients, such as fillers e.g. lactose, sucrose, mannitol, maize starch, microcrystalline cellulose or calcium hydrogen phosphate; lubricants e.g. stearic acid, polyethylene glycol, magnesium stearate, talc or silica; disintegrants e.g. rice, potato or maize starch, sodium starch glycollate or croscarmellose sodium (croscarmellose sodium is the British Approved Name for crosslinked carboxymethylcellulose); binding agents e.g. pregelatinised maize starch, polyvinylpyrrolidone or hypromellose (hypromellose is the British Approved Name of hydroxypropyl methylcellulose) and wetting agents.

The compositions of the present invention always contain large amounts of brewer's yeast.

Brewer's yeast throughout this application means in fact the product of the autolysis and hydrolysis of brewer's yeast. Said autolysed and hydrolyzed product can, for instance, be obtained in the following manner. *Saccharomyces cerevisiae* used in breweries is separated after the brewing process from the residual grain. Said yeast is first heated and pumped into an autolysis tank. During the autolysis the yeast's own enzymes break down the cell wall as well as the yeast proteins. After said autolysis the yeast is again heated to inactivate any remaining enzymes. Following the inactivation the yeast is centrifuged to collect the cell wall material. Said cell wall material is then pasteurized and spray dried, after wich the product is completely hydrolyzed with hydrochloric acid and then neutralized with sodium hydroxide. The remaining product is then again pasteurized and spray dried.

Interesting fillers are lactose, sucrose or microcrystalline cellulose; preferably lactose and microcrystalline cellulose. Interesting lubricants are stearic acid, polyethylene glycol, hydrogenated vegetable oil, sodium stearyl fumarate or magnesium stearate, preferably magnesium stearate. Interesting disintegrants are rice, potato or maize starch, preferably croscarmellose sodium. Preferred binding agent is hypromellose. Several grades of hypromellose are available. Preferred grade of hypromellose is hypromellose 2910 15 cps (The grades of hypromelllose are distinguished by a four digit code, here 2910. The first two digits represent the approximate percentage composition of methoxyl groups, and the third and fourth digits the approximate percentage composition of hydroxypropyl groups. The indication "15 cps" refers to the viscosity of 15 centipoise (15 mPa.s) of a 2% solution measured at 20° C.

Interesting compositions contain from 20% to 40% by weight of active ingredient, more interesting compositions comprise about 21% up to 35% by weight of the active ingredient. Preferably the active ingredient is present in about 22% by weight.

Brewer's yeast is present in amount from 40% to 70% by weight. Interesting compositions comprise from 45% to 70% by weight of brewer's yeast. Preferably the brewer's yeast is present in about 50% by weight.

A binder may be absent or may be present up to an amount of 4%. Preferably, the binder is hydroxypropyl methylcellulose in an amount of about 2.5%.

Fillers may be absent or present in an amount up to 25%. Preferably said filler is a carbohydrate derivative such as sorbitol or cellulose, especially microcrystalline cellulose. Mixtures of said carbohydrate derivatives may also be present.

Wetting agents may be absent or present in an amount up to 0.5% by weight. Preferred wetting agent is sodium lauryl sulphate.

Lubricants are present in an amount from 0.1% to 1.5% by weight. Preferred lubricant is magnesium stearate.

Flavouring agent may be present in an amount from 0.001% to 0.5% by weight. Said flavouring agents are commercially available. Preferred flavouring agents are meat flavours. Meat flavours are commercially available as additives for pet feed.

Interesting compositions comprise by weight based on the total weight of the composition.

flubendazole: from 20% to 40%
brewer's yeast: from 40% to 70%
fillers: from 0% to 25%
binding agents: from 0% to 4% flavouring agents: from 0.001% to 0.5%
wetting agents: from 0% to 0.5%
lubricants: from 0.1% to 1.5%

More interesting compositions comprise by weight based on the total weight of the composition.

flubendazole: from 21% to 35%
brewer's yeast from 45% to 70%
fillers: from 0% to 25%
binding agents: from 0% to 4%
flavouring agents: from 0.001% to 0.5%
wetting agents: from 0% to 0.5%
lubricants: from 0.1% to 1.5%

Preferred compositions comprise by weight based on the total weight of the composition.

flubendazole: from 22% to 33%
brewer's yeast: from 50% to 65%
hydroxypropyl methylcellulose: from 2% to 3%
flavouring agents: from 0.1% to 0.2%.

The compositions may be prepared by intimately mixing the ingredients.

One way of preparing the compositions according to the invention is to blend flubendazole with the suitable excipients and to granulate said blend.

According to the present invention the composition is in the from of a tablet, preferably a chewable tablet.

Tablets according to this invention may be right circular cylinders, the end surfaces of which may be flat or convex and the level edged. Said tablets may have lines or breakmarks and may bear a symbol or other markings.

The tablets according to the present invention also should have an appropriate strength. An appropriate strength is defined as exceeding 100 N (Newton). Said tablets have a thickness of about 4.5 mm.

The tablets of the present invention are preferable packaged in impermeable package, e.g. Tristar, which is a laminate van polyvinyl chloride, polyethylene and polyvinylidene chloride.

As is shown in example 3 hereinunder almost 90% of the dogs (of different breeds) readily accepted the tablets of the above composition.

A further aspect of the present invention provides a method of treating companion animals, especially dogs suffering from helminthiasis which comprises the administration of a chewable tablet containing flubendazole. It will be appreciated that the precise therapeutic dose of the active ingredient will depend on the age and the condition of the animal and the nature of the condition to be treated and will be at the ultimate discretion of the attendant veterinary.

However, in general effective doses of the treatment of helminthiasis in companion animals, will lie in the range of 5 mg/kg to 50 mg/kg body weight.

EXAMPLE 1

Preparation of the binder solution 150 g of Hypromellose 2910 15 cps and 18 g of sodium lauryl sulphate were dissolved in 3400 ml demineralized water under stirring.

Preparation of the granulate 1.320 g of flubendazole, 60 g colloidal silicon dioxide en 3002 g brewer's yeast are mixed in a fluidized-bed granulator until a homogenous mixture is obtained. Subsequently, the binder solution is sprayed onto the powder mixture during continued mixing. After the spraying the granulate is dried with an inlet air temperature being 75° C.

Preparation of the compression mixture

The dried granulate, 750 g microcrystalline cellulose, 660 g of crystalline sorbitol and 30 g of magnesium stearate are sieved and are mixed in a planetary powder mixer until a homogenous mixture is obtained.

Preparation of the tablets

From the above compression mixture tablets of 1000 mg are prepared using a rotatory tablet press.

EXAMPLE 2

According to analogous processes as mentioned above the following tablets were prepared.

| ingredient | composition | | | | |
|---|---|---|---|---|---|
| | A quantity (in mg) | B quantity (in mg) | C quantity (in mg) | D quantity (in mg) | E quantity (in mg) |
| flubendazole | 330.0 | 330.0 | 220.0 | 220.0 | 220.0 |
| brewer's yeast | 616.3 | 500.0 | 577.9 | 500.4 | 500.4 |
| colloidal silicon dioxide | — | — | 9.5 | 10.0 | 10.0 |
| hypromellose 2910 15 cps | — | — | 23.8 | 25.0 | 25.0 |
| sodium laulylsulphate | — | 2.9 | 2.9 | 3.0 | 3.0 |
| sorbitol crystalline | — | — | 105.0 | 110.0 | 110.0 |
| sorbitol 70% | — | 107.2 | — | — | — |
| meat flavour | 0.5 | 0.5 | 1.5 | 1.6 | 1.6 |
| magnesium stearate | 3.3 | 9.5 | 9.5 | 10.0 | 5.0 |
| microcrostalline cellulose | — | — | — | 120.0 | 125.0 |
| total weight of the tablet | 950.0 | 950.0 | 950.0 | 1000.0 | 1000.0 |

EXAMPLE 3

A total number of 119 dogs of 40 different breeds with body weights ranging from 5 to 80 kg (average 27 kg) were used in this experiment. The tablets used in this experiment had composition E (see example 2). In 66 dogs (55%) the time of administration of the tablets had no connection with the meal. From the remaining 53 dogs, 38 were treated before meal, 2 dogs during their meal and 13 dogs got the tablets after their meal. In 68 dogs the usual diet consisted of only 1 type of food: either canned food (31 dogs), or dry food in different kinds of presentations (16 dogs), or home prepared meal (21 dogs). The diet of the remaining 51 dogs was of mixed nature: canned and dry food (3 dogs), canned and home prepared meal (23 dogs), dry and home prepared meal (24 dogs) and canned, dry and home prepared meal (1 dog). 103 dogs (86.5%) accepted the flubendazole tablets readily whereas 16 dogs (13.5%) refused the tablets. The palatability was not connected with the breed, the composition of the diet or the time of administration of the flubendazole chewable tablets.

We claim:

1. An anthelmintic composition palatable to companion animals which consists essentially of flubendazole and brewer's yeast.

2. A composition according to claim 1 wherein said companion animals are dogs.

3. A composition according to claim 1 wherein the amount of brewer's yeast ranges from 40% to 70%.

4. A composition according to claim 1 comprising by weight based on the total weight of the composition:

flubendazole: from 20% to 40%
brewer's yeast: from 40% to 70%
fillers: from 0% to 25%
binding agents: from 0% to 4% flavouring agents: from 0.001% to 0.5% wetting agents: from 0% to 0.5% lubricants: from 0.1% to 1.5%.

5. A composition according to claim 4 comprising by weight based on the total weight of the composition:

flubendazole: from 22% to 33% brewer's yeast: from 50% to 65% hydroxypropyl methylcellulose: from 2% to 3% flavouring agents: from 0.1% to 0.2%.

6. A composition according to claim 5 wherein said composition is in the form of a chewable tablet.

7. A chewable tablet according to claim 6 wherein said tablet has the following composition:

flubendazole: 220.0 mg 22.00% brewer's yeast: 500.4 mg 50.04% colloidal silicon dioxide: 10.0 mg 1.00% hypromellose 2910 15 cps: 25.0 mg 2.50% sodium lauryl sulphate: 3.0 mg 0.30% sorbitol crystalline: 110.0 mg 11.00% meat flavour: 1.6 mg 0.16% magnesium stearate: 5.0 mg 0.50% microcrystalline cellulose: 125.0 mg 12.50%.

\* \* \* \* \*